(12) United States Patent
Fanson et al.

(10) Patent No.: US 7,582,586 B2
(45) Date of Patent: Sep. 1, 2009

(54) SUPPORTED CATALYSTS WITH CONTROLLED METAL CLUSTER SIZE

(75) Inventors: Paul T. Fanson, Brighton, MI (US); Hirohito Hirata, Nagaizumi (JP); Michael D. Amiridis, Columbia, SC (US); Christopher T. Williams, Columbia, SC (US); David S. Deutsch, Columbia, SC (US); Attilio Siani, Cayce, SC (US); Shinichi Matsumoto, Tougou-Cho (JP)

(73) Assignees: Toyota Motor Corporation, Toyota (JP); Toyotal Motor Engineering & Manufacturing North America, Inc., Erlanger, KY (US)

( * ) Notice: Subject to any disclaimer, the term of this patent is extended or adjusted under 35 U.S.C. 154(b) by 148 days.

(21) Appl. No.: 11/466,900

(22) Filed: Aug. 24, 2006

(65) Prior Publication Data
US 2008/0051282 A1    Feb. 28, 2008

(51) Int. Cl.
*B01J 31/00*    (2006.01)
*B01J 37/00*    (2006.01)
*B01J 21/00*    (2006.01)
*B01J 23/42*    (2006.01)
*B01J 23/44*    (2006.01)
*C08F 4/60*    (2006.01)
*C08F 4/02*    (2006.01)
*B01J 23/40*    (2006.01)
*B01J 23/10*    (2006.01)
*B01J 23/00*    (2006.01)

(52) U.S. Cl. .............. 502/185; 502/162; 502/167; 502/261; 502/304; 502/327; 502/349; 502/350

(58) Field of Classification Search .................. 502/162, 502/167, 261, 339, 185, 327, 304, 349, 350
See application file for complete search history.

(56) References Cited

U.S. PATENT DOCUMENTS 6,288,253 B1 *   9/2001   Manzer et al. .................. 556/9

(Continued)

OTHER PUBLICATIONS

"Dendrimer templates for heterogeneous catalysts: Bimetallic Pt-Au nanoparticles on oxide supports," Bethany J. Auten et al. Applied Catalysis B: Environmental 81 (2008), pp. 225-235.*

(Continued)

*Primary Examiner*—Patricia L Hailey
(74) *Attorney, Agent, or Firm*—Gifford, Krass, Sprinkle, Anderson & Citkowski, P.C.

(57) ABSTRACT

There is disclosed a process for producing a catalyst. The process includes the steps of: a) combining a dendrimer polymer and metal salt in solution forming a metal ion complex; b) exposing the metal ion complex to a reducing environment forming a dendrimer metal nanocomposite; c) depositing the dendrimer metal nanocomposite onto a catalyst support material; d) removing a solvent from the dendrimer metal nanocomposite forming metal clusters; and e) removing the dendrimer polymer forming a catalyst. Additionally, there is disclosed a catalyst having a catalytic metal deposited on a substrate. The catalytic metal is formed in clusters having a size of from 2 to 150 atoms. In another aspect, the clusters may have a spacing of from 2 to 100 nanometers between adjacent metal clusters. Further, in another aspect, the metal clusters which comprise the catalyst have a size distribution in which 70% of the clusters are within 0.6 nm of the average diameter and 99% of the particles are within 1.5 nm of the average diameter.

25 Claims, 4 Drawing Sheets

U.S. PATENT DOCUMENTS 6,645,444 B2 * 11/2003 Goldstein ............... 423/1
6,660,680 B1 12/2003 Hampden-Smith et al.
7,160,525 B1 * 1/2007 Peng et al. ............... 423/1
7,374,599 B1 * 5/2008 Shelnutt et al. ........... 75/370

OTHER PUBLICATIONS

"Electrodeposition of Pt nanoclusters on the surface modified by monolayer poly(amidoamine) dendrimer film," Lei Qian et al. Electrochemistry Communications 7 (2005), pp. 1209-1212.*

"Partial hydrogenation of 1,3-cyclooctadiene using dendrimer-encapsulated Pd-Rh bimetallic nanoparticles," Young-Min Chung et al. Journal of Molecular Catalysis A: Chemical 206 (2003), pp. 291-298.*

Dendrimer-Mediated Immobilization of Catalytic Nanoparticles on Flat, Solid Supports; Li Sun and Richard Crooks, Department of Chemistry, Texas A & M University; Jul. 25, 2002.

Synthesis, Characterization, and Surface Immobilization of Platinum, and Palladium Nanoparticles Encapsulated within Amine-Terminated Poly(amidoamine) Dendrimers; Herchang Ye, Robert W.J. Scott, and Richard M. Crooks; Department of Chemistry Texas A & M University; Jan. 5, 2004.

Dendrimer-Encapsulated Metal Nanoparticles: Synthesis, Characterization, and Applications to Catalysis; Accounts of Chemical Research; vol. 34, No. 3; Mar. 2001; Richard M. Crooks, Minggi Zhao, Li Sun, Victor Chechik and Lee Yeung.

Dendrimer-Encapsulated Pt Nanoparticles: Synthesis, Characterization, and Applications to Catalysis; Minggi Zhao and Richard Crooks; Advanced Materials 1999, 11, No. 3.

Lafaye et al.; Particle Size Control in Dendrimer-Derived Supported Ruthenium Catalysts; American Chemical Society; Mar. 2006; pp. 7725-7731.

Deutsch et al.; Decomposition and activation of Pt-dendrimer nanocomposites on a silica support; Catalysis Letters; vol. 97; Nos. 3-4; pp. 139-143; Sep. 2004.

Lafaye et al.; Synthesis and microscopic characterization of dendrimer-derived Ru/Al$_2$O$_3$ catalysts; Catalysis Letters; vol. 96; Nos. 1-2; pp. 43-47; Jul. 2004.

* cited by examiner

SUPPORTED CATALYSTS WITH CONTROLLED METAL CLUSTER SIZE

FIELD OF THE INVENTION

The invention relates to catalysts and a process for producing catalysts.

BACKGROUND OF THE INVENTION

Traditional methods for synthesizing heterogeneous catalysts often involve the deposition of an inorganic salt precursor onto a porous support via incipient wetness impregnation or co-precipitation techniques, followed by various drying and post-deposition steps. Attempts to control the size of the resulting metal particles are often made through the optimization of precursor solution conditions and subsequent time/temperature thermal treatments. However, the results of such preparation methods often include poor control over metal particle size, geometry, and metal dispersion. The above referenced techniques lack the ability to precisely control the particle size, particle spacing, and size distribution of particles in a catalyst.

There is therefore, a need in the art for a catalyst with a tightly controlled particle size, spacing and distribution. There is additionally a need in the art for a process for producing the catalyst.

SUMMARY OF THE INVENTION

There is disclosed a process for producing a catalyst. The process includes the steps of: a) combining a dendrimer polymer and metal salt in solution forming a metal ion complex; b) exposing the metal ion complex to a reducing environment forming a dendrimer metal nanocomposite; c) depositing dendrimer metal nanocomposite onto a catalyst support material; d) removing a solvent from the dendrimer metal nanocomposite forming metal clusters; and e) removing the dendrimer polymer forming a catalyst.

Additionally, there is disclosed a catalyst having a catalytic metal deposited on a substrate. The catalytic metal is formed in clusters having a size of from 2 to 150 atoms. In another aspect, the clusters may have a spacing of from 2 to 100 nanometers between adjacent metal clusters. Further, in another aspect, the metal clusters may have a size distribution in which 70% of the clusters are within 0.6 nm of the average diameter and 99% of the particles are within 1.5 nm of the average diameter.

DETAILED DESCRIPTION OF THE PREFERRED EMBODIMENTS

Figure 6:
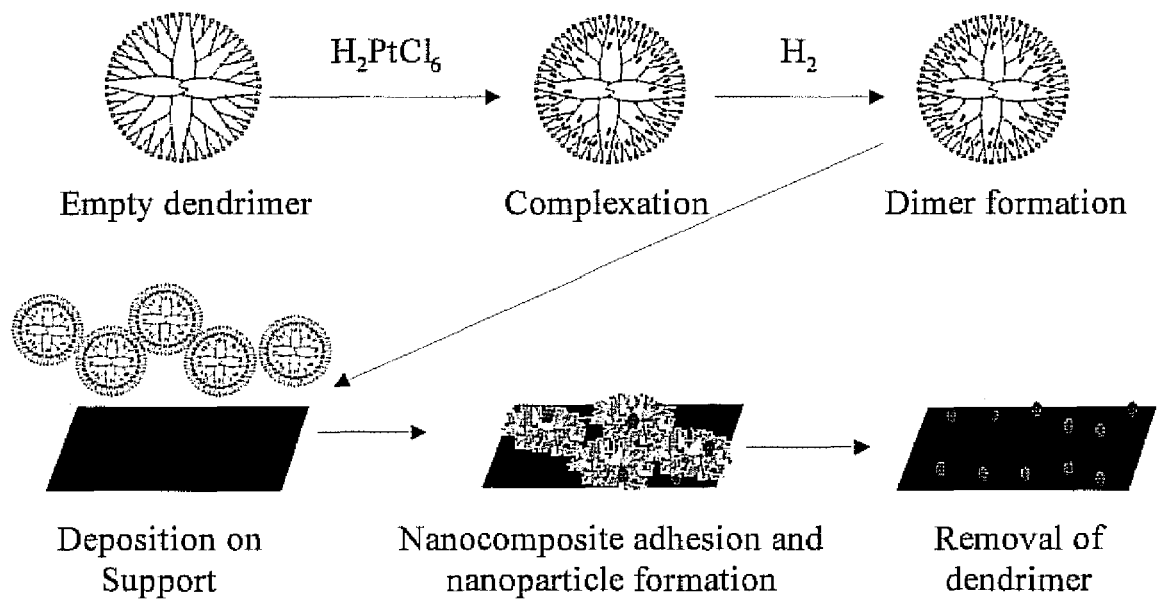
FIG. 6 is a diagram of the steps in the process of the invention.

Referring to FIG. 6, there is shown a diagram of a process for producing a catalyst. The process includes the steps of: a) combining a dendrimer polymer and metal salt in solution forming a metal ion complex, b) exposing the metal ion complex to a reducing environment forming a dendrimer metal nanocomposite, c) depositing the dendrimer metal nanocomposite onto a catalyst support material, d) removing a solvent from the dendrimer metal nanocomposite forming metal clusters, and e) removing the dendrimer polymer forming a catalyst.

Various dendrimer polymers may be used in the process for producing a catalyst. In one aspect, G3, G4, and G5 poly amido amine polymers or PAMAM polymers may be used by the process. Heterogeneous catalyst synthesis through the use of dendrimer metal nanocomposites utilizes an atom up design for size and compositional control of active metal nanoparticles. Additionally, the number of sites for metal dendrimer complexation varies by the generation of polymer utilized, thus making it possible to tune the number of metal atoms per nanoparticle housed within the dendrimer. These properties of PAMAM dendrimers allow for the synthesis of dendrimer metal nanocomposites or DMNs of different metals with narrow particle size distributions having an average particle size in the nanoscale range.

Various catalytic metals may be combined with the dendrimer polymer. The metal salts may be of any catalytic metal and in one aspect may be selected from platinum, rhodium and palladium salts. It should be realized that other catalytic metals such as copper, gold, silver, iron, ruthenium, iridium and other known catalytic metal elements may be utilized by the process.

Various catalytic support materials may be utilized by the process. The catalytic supports may include various metal oxides including aluminum oxide, magnesium oxide, cerium oxide, zirconium oxide, silicon dioxide and titanium dioxide etc., a mixture and/or solid solution of two or more oxides selected from these oxides as well as activated carbon. The supports provide a stable substrate onto which the metal particles may be dispersed forming a stable catalyst.

In the first combining step a), a molar ratio of the metal salt to dendrimer polymer is maintained such that a desired loading of metal in the resulting metal ion complex is maintained. Various parameters including the size of the metal clusters as well as the desired final spacing between the metal clusters may be considered when combining the dendrimer polymer and metal salt in solution forming the metal ion complex. In one aspect, the metal loading in the metal ion complex is from 10 to 20 metal atoms per dendrimer polymer structure. Additionally, the ideal spacing between the clusters was controlled to a level of greater than 4.5 nm by using a G4 dendrimer.

In the combining step, the metal salt and dendrimer polymer solutions are combined under an inert atmosphere and stirred for a sufficient period of time to form the metal ion complex. Various combinations of metal salts and dendrimer polymers may require various times to form a metal ion complex.

In the next step of the process, the metal ion complex is exposed to a reducing environment to form a dendrimer metal nanocomposite. In one aspect, a reducing agent may be added to the metal ion complex. Suitable reducing agents include hydrogen and sodium borohydride. In one aspect, the reducing agent may be added in an amount such that a ratio of anion of the reducing agent to cation of the metal in the metal ion complex is 8:1. The metal ion complex may be exposed to the reducing environment for various periods of time and at various concentrations of reducing agent. Additionally, hydrogen gas may be bubbled through the solution to expose the metal ion complex to a reducing agent.

Following the reduction step, the dendrimer metal nanocomposite formed by the reducing environment is deposited onto a catalytic support material. As described above, various support materials maybe used with the various metals described above. In one aspect, the dendrimer metal nanocomposite is deposited onto the substrate using a wet impregnation technique. When depositing the dendrimer metal nanocomposite onto the catalytic substrate, additional dendrimer polymer may be added to the dendrimer metal nanocomposite to facilitate a uniform spacing of metal clusters on the formed catalyst. Additionally, the dendrimer metal nanocomposite and support material may be combined such that the catalyst produced by the process has a metal content of from 0.01 wt % to 50 wt % based on a total weight of the final catalyst.

Following the deposition of the dendrimer metal nanocomposite onto the catalytic substrate, solvent in the solution of the catalyst substrate and the dendrimer metal nanocomposite is stirred such that the solvent is allowed to evaporate. The evaporation of the solvent allows the dendrimer metal nanocomposite to collapse forming the metal clusters.

Following the formation of the metal clusters, the dendrimer polymer is removed forming a catalyst. In one aspect, the removal step e) of the dendrimer polymer includes exposing the dendrimer metal nanocomposite to an oxidizing environment at an elevated temperature followed by exposure to a reducing environment at an elevated temperature. In one aspect, the oxidation step includes exposing the dendrimer metal nanocomposite to an oxygen and helium environment at a temperature of from 300° to 500° Celsius for a desired time period. Additionally, the reduction step following the oxidation step may include exposing the dendrimer metal nanocomposite to a hydrogen atmosphere at a temperature of from 200° to 400° Celsius for a desired time period. As stated above, various time periods and specific temperatures may be utilized by the process and will vary depending on the catalytic metal and dendrimer polymer used in the process.

In another aspect, there is disclosed a catalyst that includes a catalytic metal deposited on a substrate. The catalytic metal is formed in clusters having a size of from 2 to 150 atoms. Additionally, the catalytic metal clusters have a spacing of from 2 to 100 nanometers between adjacent metal clusters. Such tightly controlled spacing of metal clusters on a catalytic substrate allows for tight a catalyst that behaves in a more predictable manner and that may be resistant to deterioration in comparison to current prior art catalysts that have uneven spacing and various size distribution of metal particles within a catalyst. In another aspect, a catalyst includes a catalytic metal disposed on a substrate. The catalytic metal clusters may have a size distribution in which 70% of the clusters are within 0.6 nm of the average diameter and 99% of the particles are within 1.5 nm of the average diameter.

As outlined above, the size distribution is narrow in comparison to current catalysts such that various narrowly formed metal clusters can be specifically deposited onto a substrate material.

EXAMPLES

Hydroxyl-terminated third-(G3OH), fourth-(G4OH), and fifth-(G5OH) generation poly(amidoamine) (PAMAM) dendrimers in a methanol solution were obtained from Aldrich. Prior to use, the methanol was removed under $N_2$ flow at room temperature, and the resulting viscous polymer was diluted with deionized water. 18 MΩ·cm Milli-Q deionized water was used to prepare all aqueous solutions.

Various metal salt solutions including $H_2PtCl_6.6H_2O$ (99.95% purity, Alfa Aesar), $RhCl_3.xH_2O$ (Rh 38.5%-45.5% Alfa-Aesar) and $K_2PdCl_4.xH_2O$ were used as catalytic metal materials.

Two different supports were used: $\gamma$-$Al_2O_3$ (Alfa Aesar) and $ZrO_2$ (Daiichi Kigenso Kagaku Kogyo) The supports were calcined in air for 4 hours at 500° C. prior to their use.

Example 1

An appropriate amount of a $2.5 \times 10^{-2}$ M aqueous solution of $H_2PtCl_6.6H_2O$ was added under nitrogen flow to a 0.17 M aqueous solution of G4OH dendrimer in order to obtain the desired molar ratio of metal to G4OH dendrimer. The mixture was stirred under nitrogen flow for 3 days to allow for the complexation of Pt cations in the solution with the functional groups of the dendrimer. The dendrimer-Pt complexes were subsequently mixed with a freshly prepared $NaBH_4$ solution (molar ratio of $BH_4^-$ to metal cation of 8 to 1) in order to better facilitate reduction of the incorporated Pt cations. Following this step, the Pt-dendrimer metal nanocomposites were deposited onto previously calcined (in air, overnight at 500° C.) $\gamma$-$Al_2O_3$ via standard wet impregnation. The solvent was allowed to evaporate by stirring the resulting slurry at ambient conditions.

Example 2

This approach has been extended to the synthesis of Rh-dendrimer nanocomposites. Instead of 3 days of metal-dendrimer complexation, the Rh samples required only 1 day for incorporation within the dendrimer. Similarly, rhodium-dendrimer-metal nanocomposites were deposited onto a commercial $ZrO_2$ support (uncalcined). The nominal metal loading of both supported metal catalysts used in this study was 1 wt %.

Example 3

Pd-dendrimer nanocomposites have also been synthesized, and the process is identical to that of preparing Rh-dendrimer metal nanocomposites. Complexation of the palladium precursor, $K_2PdCl_4$, requires only 1 day for incorporation within the dendrimer. After reduction in solution with NaBH4, the resulting Pd-dendrimer nanocomposites were deposited onto calcined aluminum oxide.

In all of the examples, the dendrimer was removed as a final step in forming a catalyst. Various conditions for different metal, dendrimer and support materials may be used to remove the dendrimer. For example a sequential oxidation at an elevated temperature followed by a reduction at an elevated temperature may be used by the process. The temperature of the oxidation may range from 300° C. to 500° C.

for the various support materials, with various exposure times. In one aspect, the oxidation may be at 420° C. for one hour in a 10% $O_2$/He atmosphere $Al_2O_3$ and $ZrO_2$ supports and greater than 300° C. for one hour in the same atmosphere for $CeO_2$ supports. The reduction step may be at 200° C. for one hour in $H_2$ for the aluminum and zirconium oxide supports and at 300° C. for $CeO_2$ supports, again for the same period of time and atmosphere.

Figure 2:
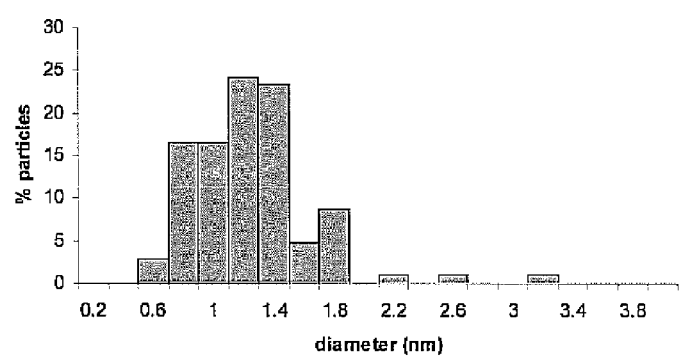
FIG. 2 shows electron microscope images of a prior art rhodium metal zirconium oxide catalyst detailing the particle distribution.
Figure 2:
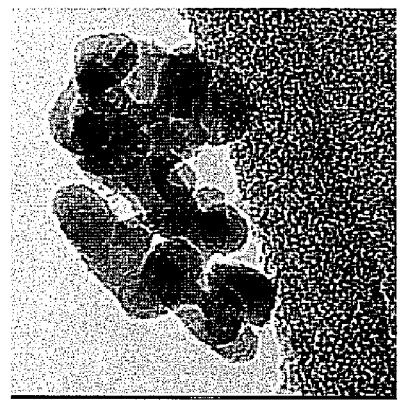
Figure 3:
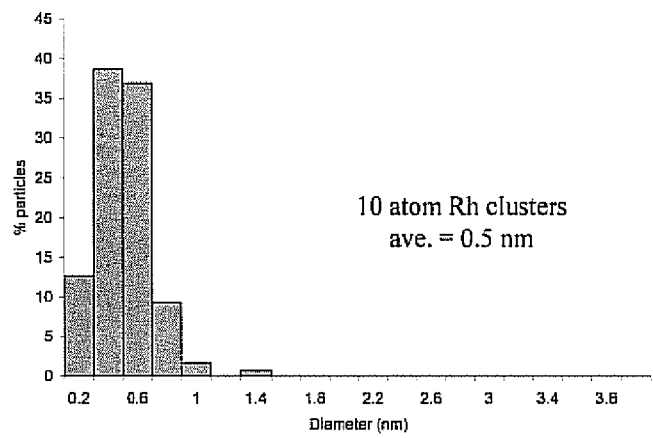
FIG. 3 shows electron microscope images of a rhodium metal zirconium oxide catalyst of the invention detailing the particle distribution.
Figure 3:
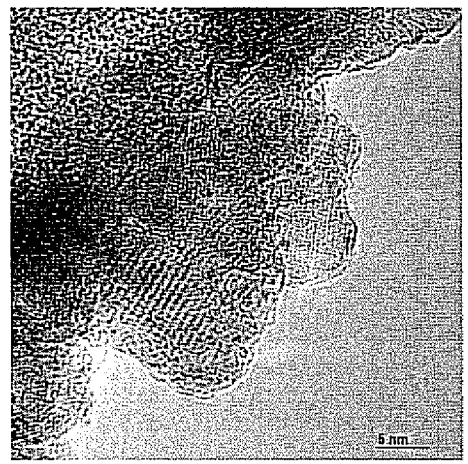
Figure 4:
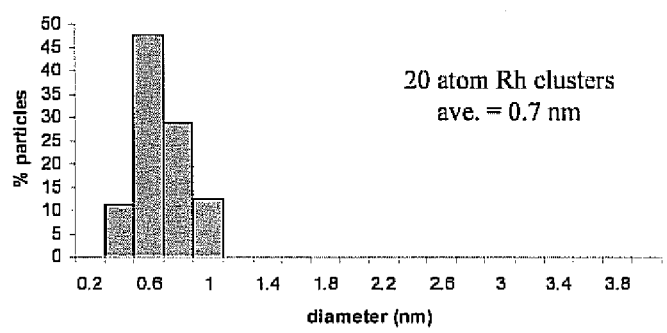
FIG. 4 shows electron microscope images of a rhodium metal zirconium oxide catalyst of the invention detailing the particle distribution.
Figure 4:
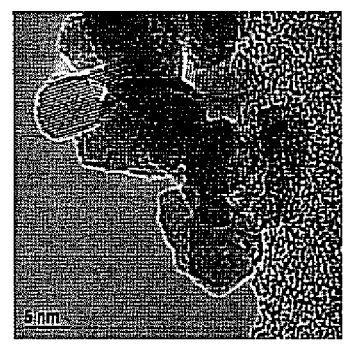
Figure 5:
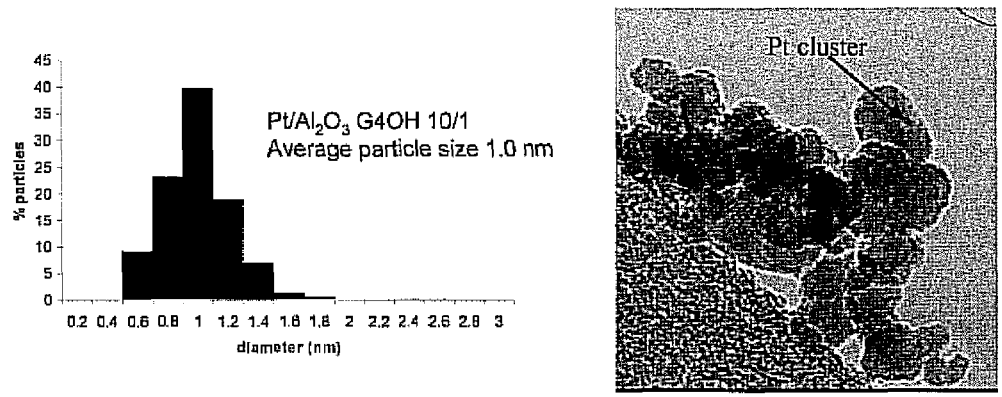
FIG. 5 shows electron microscope images of a platinum metal aluminum oxide catalyst of the invention detailing the particle distribution.

Referring to FIG. 2, there is shown a TEM image and a bar graph detailing the particle size distribution of a prior art Rh—$ZrO_2$ catalyst prepared by traditional incipient wetness impregnation. As can be seen, there is a wide distribution of particle sizes in the catalyst. In comparison, FIGS. 3 and 4 detail a Rh—$ZrO_2$ catalyst prepared as outlined above in example 2. FIG. 3 details a 10 atom Rh cluster while FIG. 4 details a 20 atom Rh cluster. As can be seen in both of the figures the particle size distribution is very narrow in comparison to the prior art catalyst of FIG. 2. Catalysts produced by the process can be tailored to meet specific size criteria with a very precise distribution of particle sizes. As with the Rh—$ZrO_2$ catalyst, the Pt—$Al_2O_3$ catalyst of FIG. 5 also displays a narrow particle size distribution.

Figure 1:
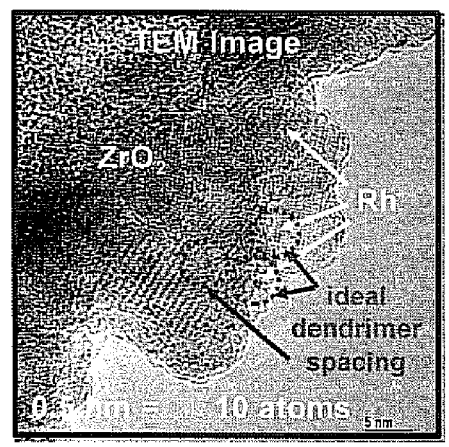
FIG. 1 shows electron microscope images of a rhodium metal zirconium oxide catalyst of the invention showing the particle spacing.

Additionally, as shown in FIG. 1, Rh clusters on a $ZrO_2$ support have a uniform spacing between adjacent metal clusters. The circles in the figure represent spacing around each of the metal clusters or dark dots in the TEM image. The spacing is from 2 to 100 nanometers between adjacent metal clusters allowing for a uniform spacing of metal clusters through out the catalyst.

Example 4

Figure 7:
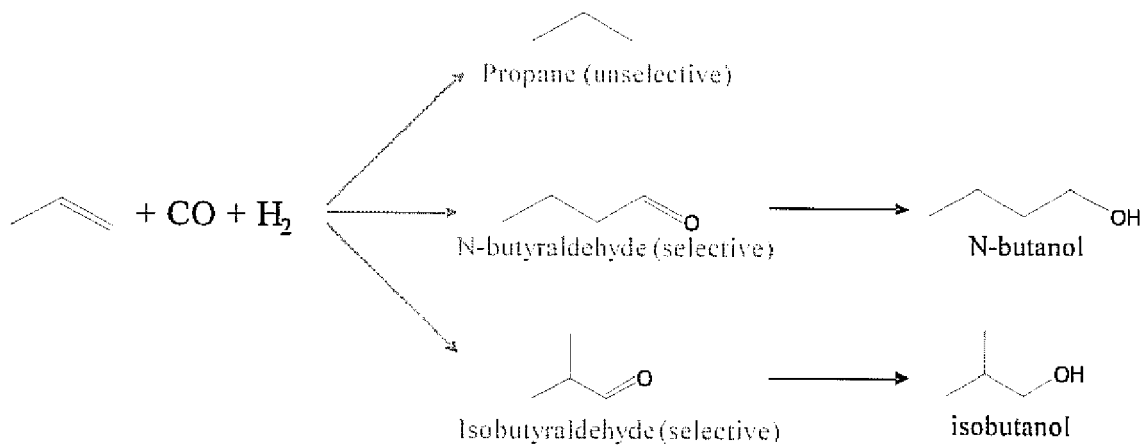
FIG. 7 is a diagram of the reaction mechanism for propylene hydroformylation.
Figure 8:
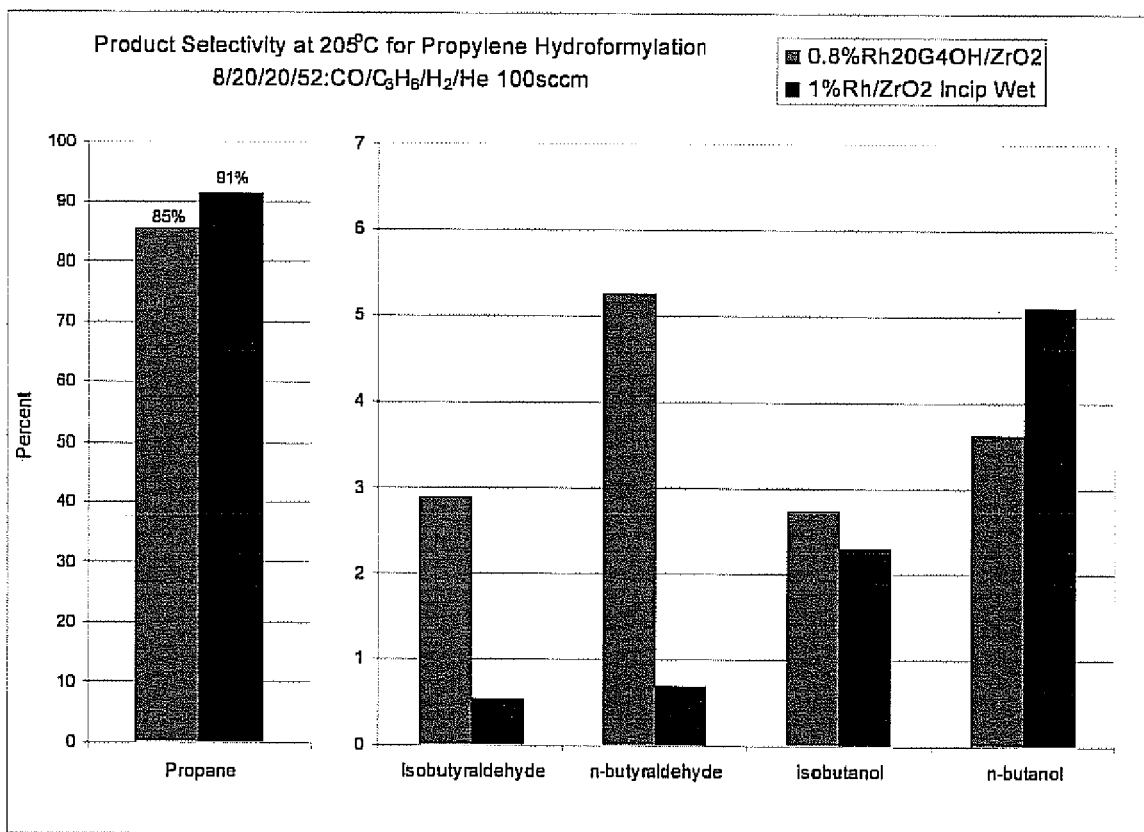
FIG. 8 is a diagram of product selectivity for propylene hydroformylation for a prior art catalyst compared to a catalyst of the invention.

A sample of a catalyst of Rh—$ZrO_2$ prepared as outlined in example 2 was compared to the prior art catalyst as described above with reference to FIG. 2 in a propylene hydroformylation reaction. The reaction is summarized in FIG. 7, showing the various products formed in the reaction. The samples used were 1 wt % Rh/$ZrO_2$ made by traditional incipient wetness impregnation and 1 wt % $Rh_{20}$G4OH/$ZrO_2$ (20 atom Rh cluster) made using G4-PAMAM dendrimer. The reaction conditions used were a fixed bed catalyst reactor at 100 psig and a temperature of from 180° C. to 250° C. 200 mg of catalyst under a flow of 100 sccm (SV=24,000 $hr^{-1}$) was used in the reaction. The reaction mixture was: 5% CO, 20% $H_2$, 20% $C_3H_6$, with the balance He. The concentration of CO in the reactor was varied as a parameter of the example. The results of the reaction for the two different samples is shown in FIG. 8. As can be seen in the figure, the selectivity of the reaction products for the two samples is different suggesting a different reaction mechanism for the two samples. At the conditions tested, the dendrimer derived catalyst showed an improved selectivity for the formation of the desired oxygenated products, 14% selectivity compared to 9% selectivity for the traditional catalyst.

Specifically, the dendrimer derived catalyst showed a significant improvement in the selectivity towards aldehydes, 8% vs. 2%. This data indicates that catalysts produced by the process may be used in various catalytic reactions to alter the selectivity of reaction products in comparison to current prior art catalysts.

While the above examples provide a description of the process of the present invention, they should not be read as limiting the process of the present invention. The invention has been described in an illustrative manner. It is to be understood that the terminology which has been used is intended to be in the nature of words of description rather than limitation. Many modifications and variations of the invention are possible in light of the above teachings. Therefore, within the scope of the appended claims, the invention may be practiced other than as specifically described.

The invention claimed is:

1. A process for forming a catalyst comprising the steps of:
   a) combining a dendrimer polymer and metal salt in solution forming a metal ion complex;
   b) exposing the metal ion complex to a reducing environment forming a dendrimer metal nanocomposite;
   c) depositing the dendrimer metal nanocomposite onto a catalyst support material;
   d) removing a solvent from the dendrimer metal nanocomposite forming metal clusters;
   e) removing the dendrimer polymer forming a catalyst wherein the catalyst has metal clusters having an average size of less than one nanometer.

2. The process of claim 1 wherein the combining step a) includes maintaining a molar ratio of metal salt to dendrimer polymer such that a desired loading of metal in the metal ion complex is maintained.

3. The process of claim 2 wherein the desired metal loading is from 2 to 150 metal atoms per dendrimer polymer structure.

4. The process of claim 1 wherein the catalyst has a metal content of from 0.01 wt% to 50 wt% based on a total weight of the catalyst.

5. The process of claim 1 wherein the metal salt and dendrimer polymer solutions are combined under an inert atmosphere and stirred for a time sufficient to form the metal ion complex.

6. The process of claim 1 wherein step b) includes adding a reducing agent selected from hydrogen or sodium borohydride.

7. The process of claim 6 wherein a ratio of anion of the reducing agent to cation of the metal in the metal ion complex is 8 to 1.

8. The process of claim 1 wherein step c) is performed using wet impregnation.

9. The process of claim 1 wherein step d) includes removing the solvent via evaporation.

10. The process of claim 1 wherein step e) includes exposing the dendrimer metal nanocomposite to an oxidizing environment at an elevated temperature followed by exposure to a reducing environment at an elevated temperature.

11. The process of claim 10 wherein the oxidation step includes exposing the dendrimer metal nanocomposite to an oxygen and helium environment at a temperature of from 300 to 500 degrees Celsius for a desired time period.

12. The process of claim 10 wherein the reduction step includes exposing the dendrimer metal nanocomposite to a hydrogen atmosphere at a temperature of from 200 to 400 degrees Celsius for a desired time period.

13. The process of claim 1 wherein the metal salt is selected from platinum, rhodium and palladium.

14. The process of claim 1 wherein the dendrimer polymer is selected from G3, G4, and G5 polyantidoamine polymers.

15. The process of claim 1 wherein the catalyst supports are selected from aluminum oxide, magnesium oxide, cerium oxide, zirconium oxide, silicon dioxide, titanium dioxide, mixture and/or solid solution of two or more oxides selected from these oxides and activated carbon.

16. A catalyst comprising:
   a catalytic metal deposited on a substrate, the catalytic metal formed in clusters having a spacing of from 2 to 100 nanometers between adjacent metal clusters wherein the metal clusters have an average size less than one nanometer.

17. The catalyst of claim 16 wherein the catalytic metal is selected from platinum, rhodium and palladium.

18. The catalyst of claim 16 wherein the substrate is selected from aluminum oxide, magnesium oxide, cerium oxide, zirconium oxide, silicon dioxide, titanium dioxide, a mixture and/or solid solution of two or more oxides selected from these oxides and activated carbon.

19. A catalyst comprising:
a catalytic metal deposited on a substrate, on which the catalytic metal clusters have a size distribution in which 70% of the clusters are within 0.6 nm of the average diameter and 99% of the particles are within 1.5nm of the average diameter and wherein the metal clusters have an average particle size of less than one nanometer.

20. The catalyst of claim 19 wherein the catalytic metal is selected from platinum, rhodium and palladium.

21. The catalyst of claim 19 wherein the substrate is selected from aluminum oxide, magnesium oxide, cerium oxide, zirconium oxide, silicon dioxide, titanium dioxide, mixture and/or solid solution of two or more oxides selected from these oxides and activated carbon.

22. A catalyst comprising:
a catalytic metal deposited on a substrate, the catalytic metal formed in clusters having an average particle size of less than one nanometer.

23. The catalyst of claim 22 wherein the catalytic metal is selected from platinum, rhodium and palladium.

24. The catalyst of claim 22 wherein the substrate is selected from aluminum oxide, magnesium oxide, cerium oxide, zirconium oxide, silicon dioxide, titanium dioxide, mixture and/or solid solution of two or more oxides selected from these oxides and activated carbon.

25. A process for forming a catalyst comprising the steps of:
a) combining a dendrimer polymer and metal salt in solution forming a metal ion complex;
b) exposing the metal ion complex to a reducing environment forming a dendrimer metal nanocomposite;
c) depositing the dendrimer metal nanocomposite onto a catalyst support material and adding additional dendrimer polymer to the dendrimer metal nanocomposite;
d) removing a solvent from the dendrimer metal nanocomposite forming metal clusters;
e) removing the dendrimer polymer forming a catalyst.

\* \* \* \* \*

UNITED STATES PATENT AND TRADEMARK OFFICE
CERTIFICATE OF CORRECTION

PATENT NO. : 7,582,586 B2 Page 1 of 1
APPLICATION NO. : 11/466900
DATED : September 1, 2009
INVENTOR(S) : Fanson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 156 days.

Signed and Sealed this

Fourteenth Day of December, 2010

David J. Kappos
*Director of the United States Patent and Trademark Office*